United States Patent [19]

Orndorff et al.

[11] Patent Number: 4,757,015
[45] Date of Patent: Jul. 12, 1988

[54] PHENYLALANINE AMMONIA LYASE-PRODUCING STRAINS

[75] Inventors: Steve A. Orndorff, Rockville; Don R. Durham, Gaithersburg, both of Md.

[73] Assignee: Genex Corporation, Gaithersburg, Md.

[21] Appl. No.: 895,389

[22] Filed: Aug. 11, 1986

[51] Int. Cl.$^4$ .................. C12P 13/22; C12N 11/00; C12N 9/88; C12N 1/16; C12R 1/645
[52] U.S. Cl. ......................... 435/108; 435/174; 435/232; 435/255; 435/911
[58] Field of Search ............... 435/108, 232, 255, 174

[56] References Cited

U.S. PATENT DOCUMENTS

| | | | |
|---|---|---|---|
| 4,574,117 | 3/1986 | Vollmer et al. | 435/108 |
| 4,584,269 | 4/1986 | Vollmer et al. | 435/108 |
| 4,584,273 | 4/1986 | Finkleman et al. | 435/232 |
| 4,598,047 | 7/1986 | McGuire | 435/108 |
| 4,636,466 | 1/1987 | McGuire et al. | 435/108 |
| 4,681,850 | 7/1987 | McGuire | 435/254 |

OTHER PUBLICATIONS

Yamada et al., *Applied and Environmental Biology* 42:773–778 (1981).
Hodgins, *J. Biol. Chem.* 246:2977–2985 (1971).
Fritz et al., *J. Biol. Chem.* 251:4646–4650 (1976).
Abell et al., *Cancer. Res.* 33:2529–2532 (1973).
Shen et al., *Science* 197:665–667 (1977).
Ambrus et al., *Science* 201:837–839 (1978).
Marusich et al., *J. Bacteriol.* 146:1013–1019 (1981).
Nakamichi et al., *Eur. J. Appl. Microbiol. Biotechnol.* 18:158–162 (1983).
Durham et al., *J. Bact.* 160:771–777 (1984).

*Primary Examiner*—Lionel M. Shapiro
*Attorney, Agent, or Firm*—Saidman, Sterne, Kessler & Goldstein

[57] ABSTRACT

Phenylalanine ammonia-lyase (PAL) producing *Rhodotorula graminis*, high PAL specific activity, strain GX 6000 its progeny, and PAL producing mutants thereof can be utilized for phenylalanine production from cinnamate. In this strain, PAL can be induced synergistically by phenylalanine and leucine or isoleucine.

8 Claims, 2 Drawing Sheets

PHENYLALANINE AMMONIA LYASE-PRODUCING STRAINS

BACKGROUND OF THE INVENTION

1. Field of the Invention

The present invention relates to an improved strain of *Rhodotorula graminis*, which is a yeast strain capable of producing phenylalanine ammonia lyase (PAL), useful for the manufacture of L- phenylalanine from t-cinnamate.

2. Brief Description of the Background Art

L-phenylalanine ammonia-lyase (PAL; EC 4.3.1.5.), is an enzyme found in several plants and also in yeast. It catalyzes the deamination of L-phenylalanine to give trans-cinnamic acid. In 1981, Yamada et al in *Applied and Environmental Biology*, 42:773-778 (1981) described the use of PAL for the rapid conversion of trans-cinnamic acid to L-phenylalanine, with a conversion yield of above 70%. This publication opened the way to investigate and apply commercially, the use of PAL for the production of phenylalanine.

The enzyme has been isolated and purified from a variety of organisms, especially the yeast *Rhodotorula glutinis* (see for example Hodgkins, *J. Biol. Chem.* 246 2977-2985 (1971), or Fritz, R. R. et al, ibid: 251: 4646-4650 (1976)).

It has been proposed that the purified enzyme is suitable for treatment of mouse neoplastic tumors (Abell, C. W., et al *Cancer Res.*, 33: 2529-2532 (1973)), the analyses of serum phenylalanine in monitoring patients with phenylketonuria (PKU) (Chen, R. et al, *Science*, 197: 665-667 (1977)), or the depletion of serum phenylalanine using immobilized PAL (Ambrus, C. M. et al., *Science*, 201: 837-839 (1978)). However, by far the greatest application of PAL to date is in the commercial production of phenylalanine from ammonia and t-cinnamate.

In 1981, Marusich, W. C. et al, *J. Bacteriol.*, 146: 1013-1019 (1981) showed that the highest specific activity of PAL could be obtained during mid exponential growth of *Rhodotorula glutinis* in a defined medium containing L-phenylalanine as the sole source of carbon. Nakamichi, K. et al., *Eur. J. Appl. Microbiol. Biotechnol.* 18: 158-162 (1983) confirmed that PAL activity in *Rhodotorula glutinis* was induced by the addition of L-phenylalanine, and showed that the activity reached a maximum after about six hours of induction and then diminished gradually. The enzyme was also induced by D-phenylalanine, L-isoleucine, D-isoleucine, L-leucine, D-leucine, L-valine, L-methionine, L-tryptophan, and L-tyrosine. When 0.1% L-isoleucine was added, high PAL activity was substained for a relatively long time. This publication also demonstrated that cells induced with isoleucine in combination with D-leucine or L-valine increased PAL specific activity over isoleucine alone.

PAL, however is also rapidly degraded in the absence of the inducer during fermentation and has a half-life of approximately 2-5 hours during fermentations of most *Rhodotorula rubra* strains.

McGuire, U.S. Pat. No. 4,598,047 shows mutant strains of *Rhodotorula rubra* (GX 5902, GX 5903, GX 5904 specifically) useful for PAL production.

*Rhodotorula graminis* wild strain GX 5007 a soil isolate, (Durham, et al., *J. Bact.* 160:771-777 (1984); this publication refers to GX 5007 as "KGX 39") has PAL activity. GX 5007 has several advantages over other production strains of *Rhodotorula rubra*. It grows 15-20% faster and requires less yeast extract, has no L-methionine requirement during induction, and PAL half-life during fermentation is about 9 hours. *R. graminis* GX 5007, however, is undesirable as a production strain due to low PAL titers obtained during fermentation.

A need therefore continues to exist for commercially useful production strains of PAL, which can be utilized in the preparation of PAL. Also, a need for ever more efficient methods of induction of PAL activity in Rhodotorula strains is needed.

SUMMARY OF THE INVENTION

The inventors, in an attempt to develop a PAL-producing strain with high titers during fermentation, fast growth and eased requirements of induction, embarked on a mutagenesis program utilizing strains of *Rhodotorula graminis* previously available to them. Out of this extensive mutagenesis program, arose a strain, *Rhodotorula graminis* GX6000 which is an over-producing PAL mutant. This strain has high PAL specific activity and titer, high PAL specific productivity, high stability and lower fermentation times to maximum PAL concentration, than any of the previously available PAL producing yeast strains. In addition, GX 6000 is also inductible by amino acids other than L-phenylalanine, and PAL synthesis and stability are not as sensitive to temperatures above 30° C. and to high oxygen tensions.

The new strain has a signicant impact on the manufacturing economics of phenylalanine from transcinnamic acid due to its high PAL stability (greater enzyme recycle, and low cost of production), the use of less expensive amino acid inducers, shorter fermentation times, less rigorous operational conditions, and higher recovery.

The present invention therefore relates to strain GX 6000, its progeny and PAL producing mutants thereof. The invention also relates to fermentation cultures comprising the above-mentioned strains, as well as methods of producing phenylalanine by using the strains and the fermentation cultures. The invention also relates to methods of inducing PAL production in such strains by using synergistic mixtures of inducers such as phenylalanine plus isoleucine, or phenylalanine plus leucine.

Also, the invention relates to methods of producing phenylalanine from cinnamate and ammonia which comprise inducing the above strains with synergistic mixtures of inducers, reacting the induced strains to produce phenylalanine from trans-cinnamic acid and ammonia, and recovering the phenylalanine.

The PAL produced by the above strains can be isolated and purified by methods known in the art and utilized for amino acid production, therapeutics or diagnostics. Cells of the PAL producing strains can also be dried and/or immobilized for production processes.

BRIEF DESCRIPTON OF THE FIGURES

BRIEF DESCRIPTION OF THE PREFERRED EMBODIMENTS

Figure 1:
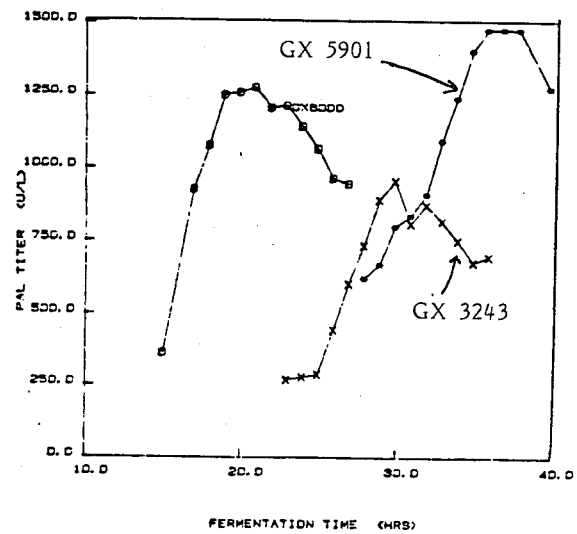
FIGS. 1 and 2 shows comparative fermentations of 3 PAL producing strains, GX6000 (invention), GX3243 and GX5901, plotting PAL titer versus time (See Example 2 for details).

The present invention extends to strain GX 6000, as well as its progeny and PAL-producing mutants thereof. The specifically isolated strain GX 6000 has been deposited at the American Type Culture Collection, Rockville, Maryland prior to the filing of this application. The deposit complies with the requirments of the Budapest Treaty. It has been given accession number ATCC 20804.

The invention is not limited to the strain on deposit, but, as noted, extends to progeny and mutants. These strains are preferably present in biologically pure cultures.

Mutants can be obtained by a variety of means. Spontaneous mutation is a common occurrence in microorganisms, and mutations can be intentionally produced by a variety of known procedures. For example, mutants can be induced using chemical, radiation and recombinant DNA techniques.

Examples of chemical mutagens are base analogues, deaminating agents, alkylating agents, and acridine derivatives.

Radiation induced mutations can be caused by such agents as ultrviolet light and X-rays. The primary mechanism by which these mutations may be caused results from excision or post-replication repair by recombination.

Additionally, mutations can also be produced by recombinant DNA techniques using restriction endonucleases. Such techniques, known as site directed mutagenesis are especially valuable to allow the deletion or insertion of large DNA fragments.

Regardless of the manner in which the mutations are induced, the important issue is that the resulting mutants produce functional PAL. In other words, the present invention includes mutants resulting in minor changes to the host such as, for example taxonomic alterations as the fermentation of certain sugars, and the like.

The *R. graminis* GX 6000 strain was isolated by a three-step procedure:

1. Ethyl methane sulfonate mutagenesis of *R. graminis* cells;
2. Selection for mutants resistant to phenylpropiolic acid, a non-metabolizable analogue of cinnamate that inhibits growth of *R. graminis* on phenylalanine but not on cinnamate, and which has been shown to inhibit PAL activity; and
3. Evaluation of resistant mutants for elevated PAL levels.

The strain Gx 6000, its progeny or mutants, can be utilized in the well-known prior art methods for the production of phenylalanine from trans-cinnamate and ammonia. See for example, U.S. Pat. Nos. 4,574,117; 4,584,269; 4,584,273; and 4,598,047, all herein incorporated by reference. See also French Pat. No. 902,314.

The strains can also be utilized as a source for the isolation and purification of PAL by known procedures. The PAL can then be utilizied by itself, or in immobilized form in producton methods of phenylalanine, in therapeutic methods for the depletion of phenylalanine in patients with PKU, in cancer therapeutics, or other known uses of the enzyme.

A typical fermentation culture for the commercial production of phenylalanine will include assimilable sources of C, N, and other essential elements, for example, yeast extract, glucose, ammonium phosphate and trace elements, as well as inducers.

After induction for an appropriate period of time, cells are separated, washed, and resuspended in reaction medium (usually water) at pH 10 to 10.5 in the presence of t-cinnamate and a source of ammonia (ammonium t-cinnamate is useful for both purposes), and allowed to catalyze the formation of phenylalanine.

After isolation of the strain and study thereof, it was further discovered that PAL induction in the strain can be carried out by the synergistic use of phenylalanine and leucine or of phenylalanine and isoleucine during fermentation. Leucine or isoleucine in any isometric form act in a synergistic manner with phenylalanine to increase the specific activity of PAL enzyme to levels 50% or greater than those observed with phenylalanine (either isomer) alone. (See Examples).

Furthermore, the highest PAL activities are obtained when using an inducer formulation with phenylalanine at a higher concentration than leucine, preferably a weight ratio of phe to leu or ile of 2-6:1, most preferably 3 or 6:1, for example, 3 g/l phenylalanine and 1 g/l leucine. Also, leucine or isoleucine are more potent inducers of PAL than phenylalanine when used singly or combination with phenylalanine, e.g. 1 g/l leucine induces a level of PAL enzyme nearly equivalent to that induced by 3 g/l phenylalanine. These phenomena have been confirmed in shake flask experiments, 2 liter fermentations, and 10 liter fermentations.

This synergistic method of induction therefore allows one to reduce the net cost of the inducer needed to obtain a given level of PAL enzyme in the strain, and provides a means of producing very high titers of PAL enzyme not obtainable through the use of L-phenylalanine alone.

In conclusion, the strains provided herein are superior phenylalanine ammonia-lyase production strains. Among some of their advantages are:

High PAL specific activity;
Little to no yeast extract requirements for maintenance energy during induction;
No amino acid (e.g., isoleucine) requirement for stabilization;
Lower L-phenylalanine requirement for induction;
Synergistic induction with L-phenylalanine and isoleucine or leucine using any combination of amino acid isomers.
High PAL stability in the fermentor and bioreactor with or without anaerobiosis;
Shorter fermentation time and shorter time for seed culture developments;
Revertants or variants do not arise; excellent culture stability and of preservation; and
Higher productivity and stability in bioreactors.

Having now generally described this invention, the same will be understood by reference to certain specific examples which are included herein for purposes of illustration only and are not intended to be limiting of the invention or of any embodiment therein.

EXAMPLE 1

Isolation of GX6000 Mutant Strain

*Rhodotorula graminis* GX 5007, a soil isolate, wild type, was grown in basal salts medium ($Na_2HPO_4$, 1.77 gm/l; $KH_2PO_4$, 1.7; $MgCl_2.6H_2O$, 0.16; $(NH_4)_2SO_4$, 0.2; $FeSO_4.7H_2O$, 0.005) containing mM glucose. The cells were cultured for 12-15 hours at 30° C. with aeration (250 rpm). An aliquot of cells (5 ml) was used to inoculate fresh medium, and growth was continued for an additional four hours. Cells were collected by centrifugation at 5,000×g for 10 minutes, washed with basal salts medium and resuspended in this medium to a volume equivalent to the original volume (25 ml). Two milliliters of cells were added separately to eight sterile tubes.

Ethylmethane sulfonate was added to each cell suspension to a concentration of 3% (v/v), and the suspensions were incubated at 30° C. with agitation (100 rpm) for either 30, 60 or 90 minutes. After the incubation period, the cells were harvested as before and washed three times with basal salts medium. Washed cells from each tube were added to separate flasks containing 25 ml of basal salts glucose medium, and grown overnight, harvested, and resuspended in one ml of basal salts medium. The cell suspensions were spread onto basal salt agar medium containing 10 mM phenylalanine and either 10 or 50 μM phenylpropiolic acid (PPA). After 3-4 days incubation at 30° C., PPA-resistant colonies of R. graminis were picked and spread onto phenylalanine agar plates containing 10 mM phenylalanine and 100 uM PPA.

Putative mutants were screened for elevated PAL specific activities as follows: PPA-resistant isolates and wild type R. graminis were grown in 25 ml of basal salts medium containing 0.1 g/l yeast extract (Difco), 5 mM glucose and 10 mM phenylalanine at 30° C. with aeration (250 rpm). Growth was followed turbidometrically with a Klett-Summerson colorimeter (no. 66 filter), and aliquots of cells were removed each hour after cells achieved a Klett reading of 150. PAL was measured by adding a sample of cells (10-100 ul) to 900 ul of a solution of 50 mM Tris buffer (pH 8.8), 25 mM L-phenylalanine, and 0.001% (wt/vol) of cetylpyridinium chloride. This mixture was incubated in a recording spectrophotometer and the appearance of cinnamic acid was followed at 280 nm (molar absorbance=16,200). The rate of increase in optical density was measured during a period of linear increase, ususally between one and five minutes after addition of cells. The ratio of the change in absorbance at 280 nm per minute to the optical density (660 nm) of the cells in the reaction mixture was used as a means to compare "specific activities" of PAL between mutants and wild type R. graminis. Over 500 PPA-resistant mutants were screened by this method. Several mutants had a higher PAL specific activity. Mutant PP-152 (GX6000) had a specific activity of 5.16 as compared to 1.70 for wild type R. graminis.

EXAMPLE 2

Comparative Fermentation Using GX6000

Strains GX3243, GX5901 (see U.S. patent application Ser. No. 673,332, filed Nov. 20, 1984, and herein incorporated by reference), and GX6000 were grown in 2 liter fermentors using the methods as follows:

1. Seed Development a. GX3243 and GX5901: From frozen stock or fresh culture inoculate 5 ml PAL Seed Medium in capped 16×150 mm tubes. Incubate on a slant at 30° C., 250 rpm for 24 hours.

Transfer the 5 ml culture to 300 ml baffled flasks containing 50 ml PAL Seed Medium. Incubate 30° C., 250 rpm for 24-30 hours.

b. GX6000: From frozen stock or fresh culture inoculate 50 ml PAL Seed Medium in 300 ml baffled flasks. Incubate at 30° C., 250 rpm for 24 hours.

c. All strains: The seed should have an $A_{660}$ greater than 40 before inoculating the fermentor.

2. Fermentor Conditions

Medium: PAL medium with 9 g/l L-phenylalanine
Volume: 1.5 liters
Inoculum: 10% (150 ml seed)
pH: Initial 6.0 Range 5.9-6.1 Titrants 2N $H_2SO_4$ and NaOH
Air flow: 1 vvm (1.5 lpm)
Mixing: 800 rpm
Temperature: 30° C.
Additions:
  (a) When initial glucose <1 g/l add 42 ml 50% glucose
  (b) When glucose again <1 g/l add 60 ml 25% Amberex 1003 and 15 ml 40 mg/ml D,L- methionine 3. Assays Turbidity: at 660 nm on Gilford Spectrophotometer
Glucose: on YSI Analyzer
Cell dry weight: uses 10 ml broth, one wash
PAL: by change in A280 using 10 μl broth to 1.5 ml Soln B 4. Media and Reagents a. PAL Seed Medium
per 1 liter:
  10.0 gm Amberex 1003
  52.5 ml HFCS
  0.1 ml SAG 5643 antifoam
  pH 6.1
b. PAL Medium
  0.5% amberex 1003
  0.2% $(NH_4)_2HPO_4$
  1.4% Glucose
  9 g/l L-phenylalanine
  0.1 ml/l SAG 5693 antifoam
  pH 6.0
c. PAL Assay Solution B
  25 mM L-phenylalanine
  50 mM Tris
  10 mg/l cetylpyridinium chloride
  pH 8.8

I. Comparisons with R. graminis Wild Strain GX5007

Table 1 shows the results.

TABLE 1

| Parameter | R. graminis | |
|---|---|---|
| | GX5007 | GX6000 |
| PAL Productivity | | |
| Specific Activity (U/gdw cells) | 26 | 75 |
| Titer (U/l) | 452 | 1,365 |
| Specific Productivity (U/gdw cells-gm L-phe) | 4.3 | 12.5 |
| Stability (h)[a] | 8 | >8 |
| Time to $PAL_{max}$ (h) | 21 | 20 |
| Maximum Cell Dry Weight (gm/l) | 17.4 | 18.2 |

[a]PAL half-life or time required for 50% decay of maximum PAL activity.

II. Comparison with R. rubra Strains

R. graminis GX6000 yielded 3-fold higher PAL activity than R. rubra GX 3243, NRRL Y-15597, a mutant of R. rubra ATCC 4056 in concurrent two liter fermentations using standard operating conditions with 6 g/l L-phenylalanine inducer (Table 2).

Figure 2:
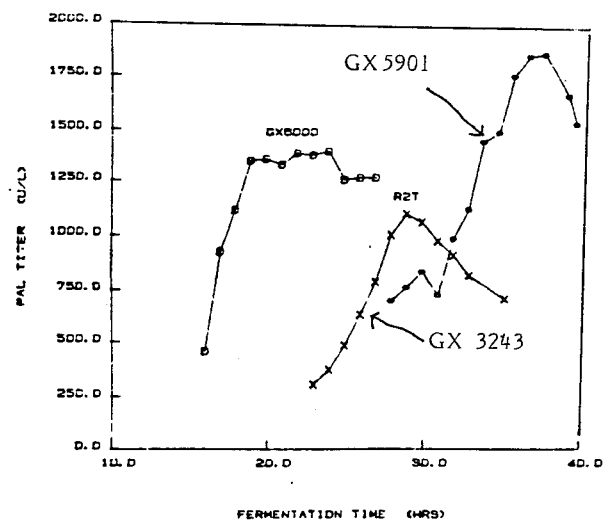

Comparison with R. rubra GX5901 is shown in Table 3. See also FIGS. 1 and 2.

TABLE 2

Comparison of R. rubra GX3243 and R. graminis GX6000 PAL fermentations[a]

| PARAMETER | GX3243 Mean | GX3243 Range | GX6000 Mean | GX6000 Range |
|---|---|---|---|---|
| PAL Activity | | | | |
| Specific Activity (U/gdw) | 28 | 14–56 | 101 | 70–130 |
| Titer (U/l) | 490 | 278–926 | 1,463 | 1,092–2,130 |
| PAL Specific Productivity (U/gdw cells - g L-phe) | 3.9 | 1.5–9.3 | 16.8 | 11.7–21.6 |
| PAL Stability (h) | 2.2 | 1–3 | 11.0 | 9.5–12 |
| Cell Dry Weight (gdw/l) | 19.3 | 16.9–20.8 | 14.8 | 12–16.9 |
| $Y_s'$ (gdw/g glc consumed) | .459 | .402–.495 | .351 | .290–.402 |
| Fermentation Time to PALmax (h) | 30 | 26–32 | 21.5 | 18–26 |
| Fermentation Runs (n) | 4 | | 11 | |

[a]Two liter fermentations using 6 g/l L-phenylalanine inducer. Operating conditions: 30° C., 1 vvm air, 800 rpm, pH 6.0 ± 0.1.

TABLE 3

Strain Comparison in Parallel Two Liter Fermentors GX5901 vs GX6000[a]

| | Strain GX5901 | Strain GX6000 |
|---|---|---|
| PAL Activity | | |
| Max Specific Activity (U/GDW) | 84.14 | 79.56 |
| Max Titer (U/L) | 1662 | 1333 |
| Hrs at Maximum PAL | 37.5 | 22.5 |
| CDW at Maximum PAL (g/l) | 19.70 | 16.78 |
| Specific Productivity (U/GDW-g Phe) | 6.23 | 5.90 |
| Biomass Yield | | |
| Max Cell Dry Weight (g/l) | 20.16 | 19.07 |
| $Y_s'$ (CDW/g glc fed) | 0.480 | 0.454 |

[a]Two liter PAL fermentations using 9 g/l L-phenylalanine inducer. Values given are a mean value of duplicate fermentations.

Two outstanding features of GX6000 compared to GX 3243 and GX 5901 are:

PAL stability—PAL activity was considerably more stable in GX6000 than R. rubra strains. PAL activity in GX6000 declined to 50% of peak levels in 11 hours whereas GX3243 reached this level in only 2.2 hours under aerated conditions at 30° C. in the fermentor. This stability is also conferred to PAL enzyme in the bioreactor, which may indicate a fundamental difference between the PAL enzymes in these strains.

Fermentation time—GX6000 took only 21.5 hours to reach peak PAL activity, whereas R. rubra strains required 30 hours. The faster growth rate of GX6000 makes seed development simple and fast, and gives a faster turnaround for the PAL fermentation.

EXAMPLE 3

Temperature Comparisons

Figure 3:
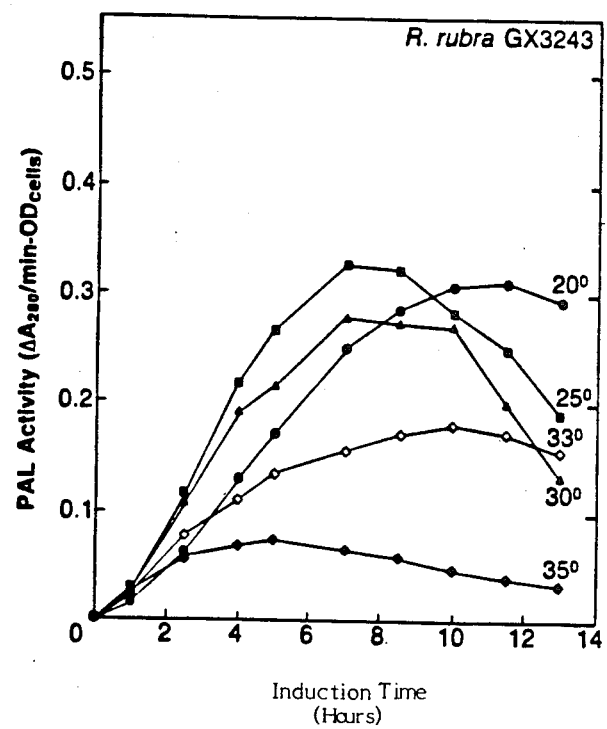
FIGS. 3 and 4 show comparison of fermentation temperatures for strains GX6000 and GX3243 (See Example 3 for details).
Figure 4:
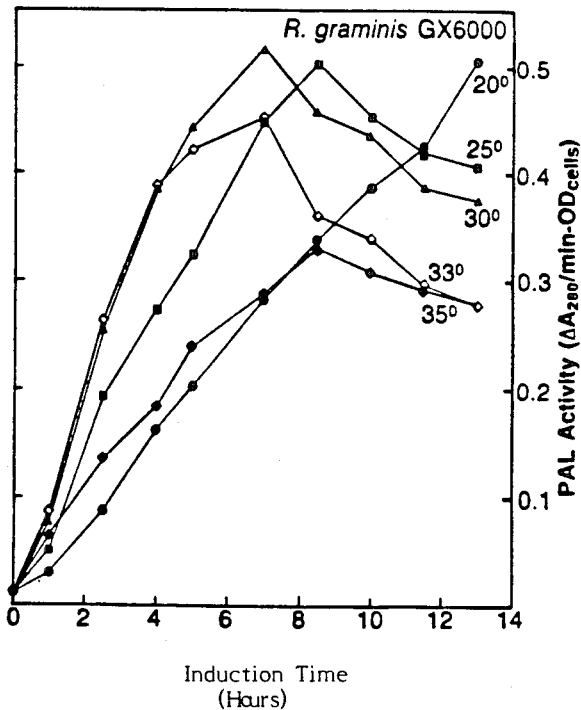

Each strain GX3243 and GX6000 was grown in basal salts medium (BSM) containing 1% yeast extract and 1% glucose for 15 hours at 30° C. in shake flasks. Washed cells were added to BSM (pH 7) and induced with 10 mM L-phenylalanine. The results are shown in FIGS. 3 and 4. They indicate that GX6000 was able to grow and express PAL activity at higher temperatures than GX3243.

EXAMPLE 4

Effect of Alternative Inducers

A variety of amino acids were tested in shake flask studies for induction of PAL with GX 6000. Test conditions were similar to those used by Nakamichi et al. supra. PAL specific activity was greatly increased over that observed with L-phenylalanine when using D,L-phenylalanine, and L-phenylalanine in combination with L-isoleucine or L-leucine (Table 4).

TABLE 4

Effect of Various Leucine and Phenylalanine Isomer Combinations on PAL Activity in R. graminis GX6000[a]

| Isomer | Maximum PAL Specific Activity (U/gdw) | Increased Specific Activity due to Leucine[b] |
|---|---|---|
| L-Leucine[c] | | |
| D, L-Phe[d] | 74.5 | 31.9 |
| L-Phe | 63.1 | 37.3 |
| D-Phe | 63.1 | 45.9 |
| D,L-Leucine | | |
| D, L-Phe | 60.2 | 17.6 |
| L-Phe | 57.3 | 31.5 |
| D-Phe | 47.3 | 30.1 |
| D, L-Leucine | 25.8 | — |
| L-Leucine | 24.4 | — |
| L-Phenylalanine | 25.8 | — |
| D-Phenylalanine | 17.2 | — |
| D, L-Phenylalanine | 42.6 | — |

[a]Shake flask assay, methods same as described in Table 5.
[b]Compared to corresponding phenylalanine isomer.
[c]Leucine isomers, 1 gm/l.
[d]Phenylalanine isomers, 6 gm/l.

D-phenylalanine also induced PAL but to levels less than those found with L-phenylalanine. Both isomers of leucine induced PAL to levels similar to those found with L-phenylalanine.

Additional shake flask tests with the combination of L-phenylalanine and L-leucine indicated that PAL activity was increased by 50% when the L-phenylalanine concentration was lowered to 3 g/l and L-leucine was added to 1 g/l. PAL activity was increased in proportion to the L-phenylalanine concentration up to 6 g/l (Table 5).

TABLE 5

Effect of L-Phenylalanine and L-Leucine Inducer Concentrations on PAL Enzyme Activity in R. graminis GX6000

| L-Phenylalanine (g/l) | L-Leucine (g/l) | Max Specific Activity (U/gdw) | Improvement |
|---|---|---|---|
| 6 | 0 | 50.3 | — |
| 0 | 1 | 50.2 | — |
| 3 | 1 | 75.4 | 50% |
| 6 | 1 | 96.4 | 93% |
| 9 | 1 | 104.7 | 109% |

[a]Shake flask test in Nakamichi et al. induction medium; pH6 30° C., CDW = 4.42 g/l.

High PAL titer and specific activity (2,6000 U/l and 149 U//gdw, respectively) were achieved when using 6 g/l L-phenylalanine and 1 g/l L-leucine in a two liter fermentor. However, unlike the shake flask test, reduced L-phenylalanine levels (<6 g/l) with 1 g/l L-leucine gave PAL activities lower than 6 g/l L-phenylalanine alone. (Table 6)

TABLE 6
Varying L-Phenylalanine Levels with Strain GX6000[a]

| Parameter | Value | | | |
|---|---|---|---|---|
| Inducer | | | | |
| L-phe (g/l) | 6 | 6 | 4 | 2 |
| L-leu (g/l) | 0 | 1 | 1 | 1 |
| PAL Activity | | | | |
| Specific Activity (U/gdw) | 129.5 | 148.7 | 111.0 | 97.3 |
| Titer (U/l) | 2130 | 2593 | 1667 | 1482 |
| PAL Specific Productivity (U/gdw-g phe) | 14.4 | 16.5 | 18.5 | 32.4 |
| Cell Dry Weight (g/l) | 16.73 | 18.15 | 15.94 | 16.04 |
| Fermentation Time | 19.5 | 19.5 | 19.5 | 19.5 |

[a]2-liter PAL fermentations
L-leucine, which is a potent synergistic inducer of PAL in GX6000 would lower the requirement for phenylalanine in the PAL fermentation.

L-leucine, which is a potent synergistic inducer of PAL in GX 6000 would never lower the requirement for phenylalanine in the PAL fermentation.

EXAMPLE 5
Bioreactor Evaluations (a) Comparison with GX3243

PAL enzyme stability observed in the fermentor was also evident in mini-bioreactor runs. PAL half-life and final PAL activity in GX 6,000 was nearly two-fold higher than GX3243 in parallel bioreactor runs (Table 7).

TABLE 7

| | PAL Activity in Bioreactors | |
|---|---|---|
| | R. rubra GX 3243 | R. graminis GX 6,000 |
| PAL Half-life (h) | 30 | 54 |
| Final PAL Activity (% of initial) | 18% | 36% |
| L-Phenylalanine Production (g/l) | 46.7 | 50.8 |
| % Conversion of Cinnamic Acid | 82% | 86% |

[a]One liter bireactors incubated at 22° C. for 88 h, sparged with nitrogen before and after sampling. Initial PAL activity = 800 U/l.

All other measures of bioreactor performance were equivalent between GX3243 and GX 6,000. In addition, a comparison of free and immobilized PAL and cell recycle in bioreactors showed that R. graminis L-phenylalanine productivity was significantly greater than R2T after recycle. L-phenylalanine productivity was also undeminished after recycle of immobilized R. graminis cells (Table 8).

TABLE 8
Effect of Cell Recycle and Immobilization on L-Phenylalanine Productivity[a]

| | GX 3243 | | R. graminis wild-type | |
|---|---|---|---|---|
| Cycle No. | Free | Immobilized[b] | Free | Immobilized[b] |
| 1 | 17[c] | 17.4 | 13.1 | 14.2 |
| 2 | 2 | 12 | 7.8 | 15.6 |

[a]Sequential, 1 liter 24 hr. mini-bioreactors.
[b]Immobilization with 2% PEI and 0.01% glutaraldehyde.
[c]Phe concentration (g/l).

Although this test was done with R. graminis wild-type, we see no reason why the mutant GX 6000 would behave differently in this capacity.

These data suggest that GX 6000 bioreactor productivity is equivalent to GX3243 but with sufficiently higher PAL stability. Thus, the total cost of catalyst per pound of product is reduced and the unit production of PAL enzyme would be reduced.

(b) Comparison with GX5901

Strains GX5901 and GX6000 were evaluated for L-phenylalanine production in duplicate bioreactor runs. Cells were obtained from 10 liter fermentations at time of peak PAL activity and batched into 1 liter bioreactors. The bioreactors were monitored over 92 hours for PAL activity and L-phenylalanine production.

Results of the bioreactor studies are summarized in Table 9.

TABLE 9
Strain Comparison in One Liter Benchtop Bioreactors GX6000 vs GX5901

| | Strain | |
|---|---|---|
| | GX5901 | GX6000 |
| L-Phe Production[a] | | |
| Final L-phe g/l | 46.4 | 46.6 |
| % Conversion | 96 | 64 |
| Rates: | | |
| Initial g phe/l-hr | 2.13 | 3.12 |
| Maximum | 2.16 | 5.56 |
| Ending | 0.18 | 0.40 |
| PAL Activity | | |
| Final % PAL Remaining | 43.2 | 66.2 |
| PAL Half-life | 50 hr | >92 hr |

[a]Values given are a mean value of duplicate bioreactor runs.

The PAL from both strains produced almost identical final L-phenylalanine titers (56 g/l), although GX5901 gave a higher conversion of cinnamic acid than GX6000.

The GX6000 cells were more stable than the GX5901 cells. Half life of the GX6000 cells was over double that of GX5901, and at the end of the runs final PAL activity of GX6000 was 36% greater than GX5901 PAL activity. The GX5901 PAL had a half-life of 50 hours, and at the end of the run 43% of the PAL activity remained. The GX6000 cells at the end of the run had 38% of the PAL activity remaining but during the course of the run 28% of the intitial catalyst had been removed. Therefore, actual activity remaining would have been 66%.

Having now fully described this invention, it will be apparent to those of ordinary skill in the art that the same can be performed by using a variety of fermentation or induction conditions, or using any of the strains within the scope of this invention, without affecting the spirit or scope of the invention as claimed in the following claims.

What is claimed is new and intended to be covered by letters patent of the United States is:

1. A *Rhodotorula graminis* strain having the identifying characteristics of strain GX 6000, its progeny or phenylalanine ammonia lyase (PAL)-producting mutants thereof.

2. The strain of claim 1 in immobilized form.

3. A fermentation culture comprising any of the strains of claim 1.

4. The fermentation culture of claim 3 which comprises an amino acid inducer selected from the group consiting of phenylalanine, leucine, isoleucine or mixtures thereof.

5. A microbiological catalytic method of producing phenylalanine from trans cinnamate and ammonia which comprises:

(1) contacting a mixture of trans cinnamate and ammonia with any of the strain of claim 1, and (2) recovering said phenylalanine.

6. A method of inducing PAL formation in a fermentation medium containing any of the strains of claim 1, which comprises adding to said fermentation medium synergistic inducing amounts of phenylalanine plus isoleucine or phenylalanine plus leucine.

7. A method of producing phenylalanine from trans cinnamate and ammonia which comprises (a) forming a fermentation culture containing any of the strains of claim 1;
(b) inducing PAL formation in such strain;
(c) contacting said strain with trans cinnamate and ammonia under conditions and for a time sufficient to catalyze the formation of phenylalanine; and
(d) recovering said phenylalanine.

8. The method of claim 7 wherein said induction is carried out with synergistic inducing amounts of phenylalanine plus isoleucine or phenylalanine plus leucine.

* * * * *